United States Patent [19]

Meguro et al.

[11] Patent Number: 4,582,839
[45] Date of Patent: Apr. 15, 1986

[54] 2,4-THIAZOLIDINEDIONES

[75] Inventors: Kanji Meguro, Nishinomiya; Takeshi Fujita, Takarazuka, both of Japan

[73] Assignee: Takeda Chemical Industries, Ltd., Osaka, Japan

[21] Appl. No.: 711,536

[22] PCT Filed: Sep. 21, 1984

[86] PCT No.: PCT/JP84/00445
§ 371 Date: Mar. 7, 1985
§ 102(e) Date: Mar. 7, 1985

Related U.S. Application Data

[63] Continuation-in-part of Ser. No. 624,689, Jun. 11, 1984, abandoned.

[51] Int. Cl.[4] .................. A61K 31/44; C07D 277/24
[52] U.S. Cl. ............................... 514/342; 546/280
[58] Field of Search ..................... 546/280, 8, 23; 514/342

[56] References Cited

U.S. PATENT DOCUMENTS 4,287,200 9/1981 Kawamatsu et al.
4,340,605 7/1982 Kawamatsu ............... 546/280

FOREIGN PATENT DOCUMENTS 0084926 8/1983 European Pat. Off. ........... 548/183

OTHER PUBLICATIONS

Sohda et al, "Studies on Anti Diabetic Agents", Chem. Pharm. Bull., Chem. Abs. 98:160624h.
Kawamatsu et al, "Thiazolidine Derivatives", Chem. Abs. 93:114506v.

Primary Examiner—Jane T. Fan
Attorney, Agent, or Firm—Wenderoth, Lind & Ponack

[57] ABSTRACT

Thiazolidinedione derivatives of the general formula:

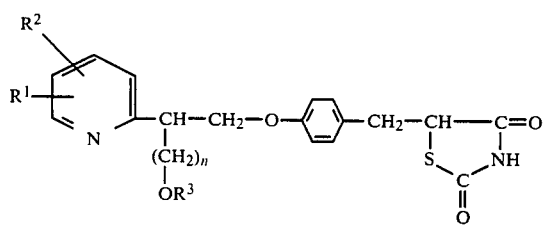

wherein $R^1$ and $R^2$ are the same or different and each represent hydrogen or a lower alkyl group; $R^3$ is hydrogen or an acyl group; n is 0 or 1 and salts thereof are novel compounds, which exhibit in mammals blood sugar- and lipid-lowering activity, and are of value as a therapeutic agent for diabetes and therapeutic agent for hyperlipemia.

8 Claims, No Drawings

2,4-THIAZOLIDINEDIONES

This is a continuation-in-part of Ser. No. 624,689, filed June 11, 1984, now abandoned.

TECHNICAL FIELD

The present invention relates to novel thiazolidinedione derivatives having blood sugar- and lipid-lowering activity, to a process for producing the same, and to pharmaceutical compositions containing the same.

BACKGROUND ART

A great variety of biguanide and sulfonylurea compounds have been conventionally employed as a therapeutic agent for diabetes. However, biguanide compounds cause lactic acidosis and therefore, are hardly used at present, while sulfonylurea compounds exhibit potent blood sugar lowering activity but often bring about serious hypoglycemia, thus requiring the precautions for use. The present inventors, after extensive research to find a compound having blood sugar lowering activity which is free from such drawbacks, discovered certain novel thiazolidinedione derivatives having excellent blood sugar- and lipid-lowering activity.

DISCLOSURE OF THE INVENTION

The present invention relates to:

1. Thiazolidinedione derivatives of the general formula:

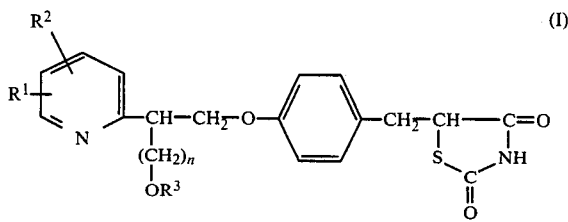

wherein $R^1$ and $R^2$ are the same or different and each represent hydrogen or a lower alkyl group; $R^3$ is hydrogen or acyl group; n is 0 or 1, 2. A process for producing thiazolidinedione derivatives of the general formula (I), characterized in that said process comprises reacting a compound of the general formula:

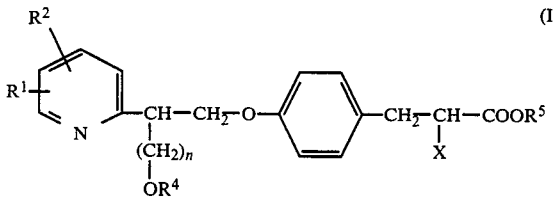

wherein $R^1$, $R^2$ and n are as defined hereinbefore; $R^4$ is hydrogen or an acyl group; $R^5$ is hydrogen or a lower alkyl group; X is a halogen atom with thiourea to produce a compound of the general formula:

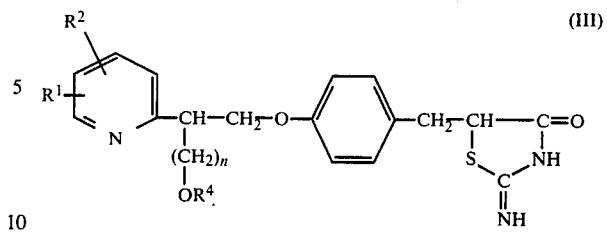

wherein each of the symbols is as defined hereinbefore and hydrolyzing the resulting compound, followed by acylating if necessary, and 3. Pharmaceutical compositions which contain thiazolidinedione derivatives of the general formula (I) or salts thereof.

With reference to the above general formulae (I), (II) and (III), examples of the lower alkyl group represented by $R^1$ and $R^2$ include lower alkyl groups having 1 to 4 carbon atoms, such as methyl, ethyl, propyl, isopropyl and butyl, preferably those having 1 to 3 carbon atoms in particular, and these may be substituted for hydrogen atoms at arbitrary positions of the pyridine ring. As the acyl group represented by $R^3$, by way of example, there may be mentioned formyl, alkylcarbonyl having 2 to 6 carbon atoms (e.g. acetyl, propionyl, butyryl, isobutyryl, pentanoyl, isopentanoyl, hexanoyl, etc.), aralkylcarbonyl having 8 to 9 carbon atoms (e.g. phenylacetyl, phenylpropionyl, etc.), arylcarbonyl having 1 to 8 carbon atoms (e.g. benzoyl, p-toluoyl, etc.). As the acyl group represented by $R^4$, there may be mentioned the same acyl groups represented by $R^3$. As the lower alkyl group represented by $R^5$, there may be mentioned the above-described lower alkyl groups represented by $R^1$ and $R^2$. Examples of the halogen atom represented by X include chlorine, bromine and iodine.

The thiazolidinedione derivatives of the general formula (I) are amphoteric compounds having acid nitrogen in the thiazolidine ring and alkaline nitrogen in the pyridine ring, and exist both in acid and base salts. Referring to salts of the thiazolidinedione derivatives (I), examples of the acid salts include inorganic acid salts, such as hydrochlorides, hydrobromides, sulfates, phosphates and methanesulfonates, and organic acid salts, such as toluenesulfonates, oxalates, malonates, maleates, fumarates, succinates, tartrates and malates, while examples of the base salts include metal salts, such as sodium salts, potassium salts, aluminum salts, magnesium salts and calcium salts.

As specific examples of the thiazolidinedione derivatives of the general formula (I) and their salts, there may be mentioned the following compounds:

5-{4-[2-Hydroxy-2-(5-methyl-2-pyridyl)ethoxy]benzyl}-2,4-thiazolidinedione,
5-{4-[2-Acetoxy-2-(5-methyl-2-pyridyl)ethoxy]benzyl}-2,4-thiazolidinedione,
5-{4-[3-Hydroxy-2-(3-methyl-2-pyridyl)propoxy]benzyl}-2,4-thiazolidinedione,
5-{4-[3-Acetoxy-2-(3-methyl-2-pyridyl)propoxy]benzyl}-2,4-thiazolidinedione,
5-{4-[3-Benzoyloxy-2-(3-methyl-2-pyridyl)propoxy]benzyl}-2,4-thiazolidinedione,
5-{4-[2-(5-Ethyl-2-pyridyl)-2-hydroxyethoxy]benzyl}-2,4-thiazolidinedione,
5-{4-[2-(5-Ethyl-2-pyridyl)-2-formyloxyethoxy]benzyl}-2,4-thiazolidinedione, 5-{4-[2-Acetoxy-2-(5-ethyl-2-pyridyl)ethoxy]benzyl}-2,4-thiazolidinedione,
5-{4-[2-(5-Ethyl-2-pyridyl)-2-propionyloxyethoxy]benzyl}-2,4-thiazolidinedione
5-{4-[2-(5-Ethyl-2-pyridyl)-2-butyryloxyethoxy]benzyl}-2,4-thiazolidinedione,
5-{4-[2-(5-Ethyl-2-pyridyl)-2-isobutyryloxyethoxy]benzyl}-2,4-thiazolidinedione,
5-{4-[2-(5-Ethyl-2-pyridyl)-2-valeryloxyethoxy]benzyl}-2,4-thiazolidinedione,
5-{4-[2-Benzoyloxy-2-(5-ethyl-2-pyridyl)ethoxy]benzyl}-2,4-thiazolidinedione,
5-{4-[2-(5-Ethyl-2-pyridyl)-3-hydroxypropoxy]benzyl}-2,4-thiazolidinedione,
5-{4-[3-Acetoxy-2-(5-ethyl-2-pyridyl)propoxy]benzyl}-2,4-thiazolidinedione,
5-{4-[2-Hydroxy-2-(2-pyridyl)ethoxy]benzyl}-2,4-thiazolidinedione,
5-{4-[2-Acetoxy-2-(2-pyridyl)ethoxy]benzyl}-2,4-thiazolidinedione,
5-{4-[2-Propionyloxy-2-(2-pyridyl)ethoxy]benzyl}-2,4-thiazolidinedione,
5-{4-[2-Benzoyloxy-2-(2-pyridyl)ethoxy]benzyl}-2,4-thiazolidinedione,
5-{4-[3-Hydroxy-2-(2-pyridyl)propoxy]benzyl}-2,4-thiazolidinedione,
5-{4-[3-Acetoxy-2-(2-pyridyl)propoxy]benzyl}-2,4-thiazolidinedione,
5-{4-[2-Hydroxy-2-(5-methyl-2-pyridyl)ethoxy]benzyl}-2,4-thiazolidinedione,
5-{4-[2-Acetoxy-2-(5-methyl-2-pyridyl)ethoxy]benzyl}-2,4-thiazolidinedione,
5-{4-[2-(5-Methyl-2-pyridyl)-2-propionyloxyethoxy]benzyl}-2,4-thiazolidinedione,
5-{4-[2-Benzoyloxy-2-(5-methyl-2-pyridyl)ethoxy]benzyl}-2,4-thiazolidinedione,
5-{4-[3-Hydroxy-2-(5-methyl-2-pyridyl)propoxy]benzyl}-2,4-thiazolidinedione,
5-{4-[2-Hydroxy-2-(3-methyl-2-pyridyl)ethoxy]benzyl}-2,4-thiazolidinedione,
5-{4-[2-Acetoxy-2-(3-methyl-2-pyridyl)ethoxy]benzyl}-2,4-thiazolidinedione,
5-{4-[2-Benzoyloxy-2-(3-methyl-2-pyridyl)ethoxy]benzyl}-2,4-thiazolidinedione,
5-{4-[2-Hydroxy-2-(4-methyl-2-pyridyl)ethoxy]benzyl}-2,4-thiazolidinedione,
5-{4-[2-Acetoxy-2-(4-methyl-2-pyridyl)ethoxy]benzyl}-2,4-thiazolidinedione,
5-{4-[2-Hydroxy-2-(4,6-dimethyl-2-pyridyl)ethoxy]benzyl}-2,4-thiazolidinedione, and
5-{4-[2-Acetoxy-2-(4,6-dimethyl-2-pyridyl)ethoxy]benzyl}-2,4-thiazolidinedione.

The reaction of a compound of the general formula (II) with thiourea is normally conducted in a solvent, such as alcohols (e.g., methanol, ethanol, propanol, 2-propanol, butanol, isobutanol, 2-methoxyethanol, etc.), dimethylsulfoxide and sulfolane. The reaction temperature normally ranges from 20° C. to 180° C., preferably from 60° C. to 150° C. The amount of thiourea to be used is 1 to 2 moles per mole of the compound (II). In this reaction, hydrogen halide is formed as a by-product as the reaction proceeds, and the reaction may be carried out in the presence of a deacidifying agent added, such as sodium acetate and potassium acetate, in order to capture such hydrogen halide. The deacidifying agent is normally used at a ratio of 1 to 1.5 moles per mole of the compound (II). By means of such reactions, the compound (III) is produced, and can be isolated, if desired, or may be subjected to the next hydrolysis step directly without isolation of the compound (III).

Hydrolysis of the compound (III) is normally carried out in an appropriate solvent and in the presence of water and a mineral acid. As the solvent, there may be mentioned such solvents as may be used in the above-described reaction of the compound (II) with thiourea. Examples of the mineral acid include hydrochloric acid, hydrobromic acid, sulfuric acid and so forth, and its amount to be used is 0.1 to 10 moles per mole of the compound (III), preferably 0.2 to 3 moles. The addition amount of water is normally a large excess amount against 1 mole of the compound (II). This reaction is normally conducted under warming or heating, and the reaction temperature is normally 60° to 150° C. The reaction time ranges normally from several hours to ten-odd hours.

By means of this reaction, there can be obtained the compound of the general formula (I) where $R^3$ is hydrogen (hereinafter referred to in some instances as "hydroxyl compound (I')").

The above-mentioned hydroxyl compound (I') may be subjected to the following acylation reaction, if necessary.

The acylation reaction of the hydroxyl compound (I') is normally carried out by the action of an acylating agent in an appropriate solvent and in the presence of a base. Examples of the said solvent include esters, such as ethyl acetate, aromatic hydrocarbons, such as benzene, toluene and xylene, ethers, such as diethyl ether, diisopropyl ether, tetrahydrofurane and dioxane, ketones, such as acetone and methyl ethyl ketone, and chlorinated hydrocarbons, such as dichloromethane, chloroform and carbon tetrachloride, as well as dimethylformamide, etc. As the acylating agent, there may be mentioned formic acid, acid anhydrides or acid halides of aliphatic, aromatic-aliphatic or aromatic carboxylic acids, and the like. Examples of the said aliphatic carboxylic acid include those having 2 to 6 carbon atoms, such as acetic acid, propionic acid, butyric acid, isobutyric acid, valeric acid, isovaleric acid and hexanoic acid, and as examples of the said aromatica-liphatic carboxylic acids, there may be mentioned those having 8 to 9 carbon atoms, such as phenylacetic acid and phenylpropionic acid, while examples of the said aromatic carboxylic acids include those having 7 to 8 carbon atoms, such as benzoic acid and p-methylbenzoic acid, whereby for example halogen (e.g., fluorine, chlorine, bromine, etc.), alkoxy (e.g., methoxy, ethoxy, etc.) and trifluoromethyl group may further be substituted for hydrogen atoms on these aromatic nuclei.

The amount of the acylating agent to be used is normally 1 to 10 moles per mole of the hydroxyl compound (I'), preferably 1 to 2 moles. Examples of the base include amines, such as pyridine and triethylamine, and carbonates and hydrogencarbonates, such as sodium carbonate, potassium carbonate, sodium hydrogencarbonate and potassium hydrogencarbonate. The base is normally used in an equimolar amount or a large excess amount against the acylating agent. In cases in which pyridine is used as a base, a large excess amount of pyridine employed can also serve as a solvent. This reaction is normally carried out at a temperature of −20° C. to 40° C., and the reaction time normally ranges from 10 minutes to 24 hours. By means of this reaction, there can be obtained the compound of the genereal formula (I) where $R^3$ is an acyl group [hereinafter referred to in some instances as "acyl compound (I")].

The thiazolidinedione derivatives (I), if necessary, can be converted into salts by reacting with acid or base in accordance with the conventional method.

The thiazolidinedione derivatives and their salts as obtained in the above manner can be isolated and purified by the known separation/purification means, such as concentration, concentration under reduced pressure, solvent extraction, crystallization, recrystallization, phase transfer and chromatography.

The compounds (I) of the present invention and their salts, in mammals (e.g., mice, dogs, cats, monkeys and man), demonstrate excellent blood sugar- and lipid-lowering activity, and in addition, are less toxic, being low both in acute and subacute toxicities; for example, 5-{4-[2-hydroxy-2-(6-methyl-2-pyridyl)ethoxy]benzyl}-2,4-thiazolidinedione, 5-{4-[3-hydroxy-2-(3-methyl-2-pyridyl)propoxy]benzyl}-2,4-thiazolidinedione, 5{-4-[2-(5-ethyl-2-pyridyl)-2-hydroxy]-benzyl}-2,4-thiazolidinedione, 5-{4-[2-(5-ethyl-2-pyridyl)-3-hydroxypropoxy]benzyl}-2,4-thiazolidinedione, 5-{4-[2-acetoxy-2-(6-methyl-2-pyridyl)ethoxy]benzyl}-2,4-thiazolidinedione and 5-{4-[3-acetoxy-2-5-ethyl-2-pyridyl)propoxy]-benzyl}-2,4-thiazolidinedione were all found to exhibit an $LD_{50}$ value of not less than 5000 mg/kg in rat when administered orally. These suggest that the thiazolidinedione derivatives (I) and their salts are useful for the treatment of hyperlipemia, diabetes and their complications. With reference to the method of administration, they are normally usable orally for example in the form of tablets, capsules, powders, granules, etc., but can also be administered parenterally in the form of injectable solutions, suppositories, pellets, etc., as the case may be. In the case of their being employed as a therapeutic agent for diabetes, they can be normally administered orally in daily doses of 0.05 mg to 10 mg/kg or parenterally in daily doses of 0.01 mg to 10 mg/kg, per adult human, and in the case of their being utilized as a therapeutic agent for hyperlipemia, they can be normally given orally in daily doses of 0.05 mg to 10 mg/kg or parenterally in daily doses of 0.01 mg to 10 mg/kg, per adult human, whereby it is desirable to administer such quantities once daily or intermittently twice to four times weekly.

The starting compound (II) of the present invention can be produced for example by the following methods.
(1) Production of the compound of the general formula (II) where n is 0;

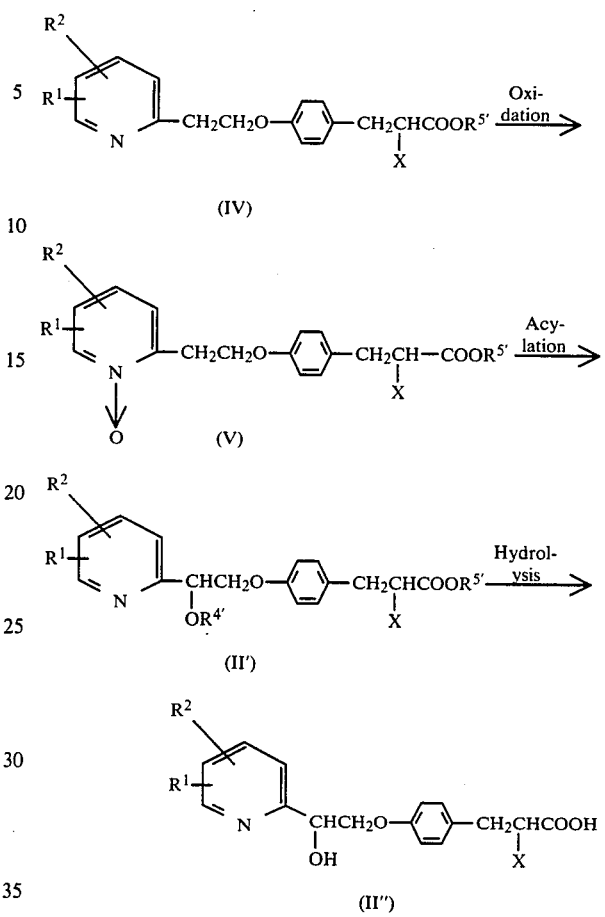

[wherein $R^1$, $R^2$ and X are as defined hereinbefore; $R^{4'}$ is as defined by the acyl group represented by $R^3$ or $R^4$; $R^{5'}$ is as defined by the lower alkyl group represented by $R^5$].

The oxidation reaction of the compound (IV) to the compound (V) can be carried out easily by reacting the compound (IV) with hydrogen peroxide or an organic peracid. Examples of such organic peracid include performic acid, peracetic acid, pertrifluoroacetic acid, perbenzoic acid, m-chloroperbenzoic acid, etc., and this oxidation reaction can be conducted in accordance with the general methods known per se. The acylation reaction of the compound (V) to the compound (II') is carried out by reacting the compound (V) with an acylating agent, and is easily conducted normally by heating with an acid anhydride or acid halide at 80° C. to 150° C. The hydrolysis reaction of the compound (II') to the compound (II") can be conducted by the ordinary method using sodium hydroxide or potassium hydroxide.

(ii) Production of the compound of the general formula (II) where n is 1:

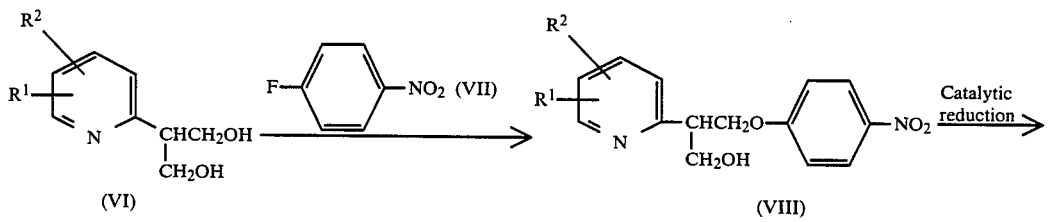

-continued

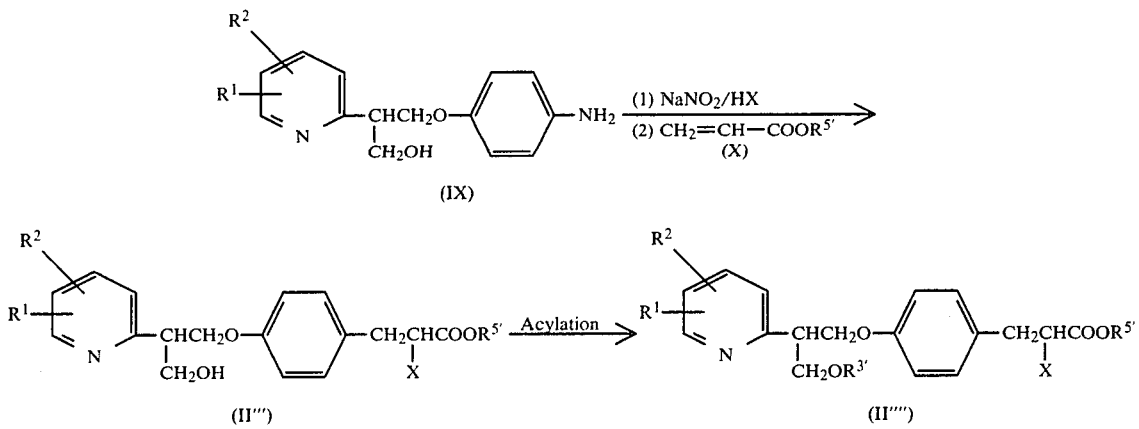

[wherein each of the symbols is as defined hereinbefore].

The reaction of the compound (IV) to the compound (VIII) is carried out by allowing the compounds (VI) and (VII) to undergo condensation in the presence of sodium hydride. This reaction can be conducted in a solvent such as diemthylformamide and tetrahydrofurane at −10° C. to 20° C. The subsequent reaction of the compound (VIII) to the compound (IX) is carried out, for example, by subjecting the compound (VIII) to catalytic reduction in the ordinary manner with use of palladium carbon as a catalyst. The reaction of the compound (IX) to the compound (II′″) is conducted by diazotizing the compound (IX) in the presence of a hydrogen halide (HX) and further subjecting the resulting the diazotized compound to the so-called Meerwein arylation reaction which involves the reaction with acrylic acid or its esters (X) in the presence of a copper catalyst (e.g., cuprous oxide, cupric oxide, cuprous chloride, cupric chloride, cuprous bromide, cupric bromide, etc.). The reaction of the compound (II′″) to the compound (II″″) is conducted by acylating the compound (II′″). This reaction can be carried out in the same manner as the procedure of acylating the above-described compound (V).

THE BEST MODE OF CARRYING OUT THE INVENTION

The examples, reference examples and experiment example are described below to illustrate the present invention more specifically, but are not intended to limit the present invention.

EXAMPLE 1

A mixture of methyl 3-{4-[2-acetoxy-2-(6-methyl-2-pyridyl)ethoxy]phenyl}-2-bromopropionate (3.2 g), thiourea (558 mg), sodium acetate (599 mg) and ethanol (30 ml) was heated under reflux for 4 hours, and then 6N-hydrochloric acid (30 ml) was added to the mixture, followed by heating under reflux for 16 hours. After neutralization with aqueous sodium hydrogencarbonate solution, the reaction mixture is extracted with chloroform, and the chloroform layer was washed with water and dried (MgSO$_4$). After the solvent was distilled off, the residue was chromatographed on a silica-gel (100 g) column and elution was effected with benzene-acetone (10:1, V/V) to give 5-{4-[2-hydroxy-2-(6-methyl-2-pyridyl)ethoxy]benzyl}-2,4-thiazolidinedione in the form of crystals. Yield of 0.95 g. Recrystallization from ethyl acetate-hexane produced colorless prisms. m.p. 154°–155° C.

Elemental analysis, for $C_{18}H_{18}N_2O_4S$: Calcd.: C, 60.32; H, 5.06; N, 7.82. Found: C, 60.53; H, 5.24; N, 7.75.

EXAMPLE 2

(1) A mixture of methyl 2-bromo-3-{4-[3-hydroxy-2-(3-methyl-2-pyridyl)propoxy]phenyl}propionate (4.7 g), thiourea (875 mg), sodium acetate (943 mg) and ethanol (50 ml) was heated under reflux for 3 hours. The mixture was diluted with water, neutralized with aqueous sodium hydrogencarbonate solution and extracted with ethyl acetate. The ethyl acetate layer was washed with water, dried (MgSO$_4$) and freed of the solvent to give 5-{4-[3-hydroxy-2-(3-methyl-2-pyridyl)propoxy]benzyl}-2-imino-4-thiazolidinone in the form of crystals. Yield of 25 g. Recrystallization from chloroform-methanol produced colorless prisms. m.p. 213°–214° C.

Elemental analysis, for $C_{19}H_{21}N_3O_3S$: Calcd.: C, 61.44; H, 5.70; N, 11.31. Found: C, 61.14; H, 5.62; N, 10.99.

(2) 5-{4-[3-hydroxy-2-(3-methyl-2-pyridyl)propoxy]benzyl}-2-imino-4-thiazolidinone (2.3 g) was dissolved in a mixture of 2N-hydrochloric acid and ethanol (20 ml), and the solution was heated under reflux for 4 hours. After neutralization with aqueous sodium hydrogencarbonate solution, the solution was extracted with chloroform, and the chloroform layer was washed with water and dried (MgSO$_4$). The solvent was distilled off to give 5-{4-[3-hydroxy-2-(3-methyl-2-pyridyl)propoxy]-benzyl}-2,4-thiazolidinedione in the form of crystals. Yield of 1.9 g. Recrystallization from ethanol produced colorless prisms. m.p. 182°–183° C.

Elemental analysis, for $C_{19}H_{20}N_2O_4S$: Calcd.: C, 61.27; H, 5.41; N, 7.52. Found: C, 61.57; H, 5.49; N, 7.74.

EXAMPLE 3

By following the same procedure as described in Example 1, methyl 3-{4-[2-acetoxy-2-(5-ethyl-2-pyridyl)ethoxy]phenyl}-2-bromopropionate (10.0 g), thiourea (2.0 g) and sodium acetate (2.2 g) were allowed to undergo reaction in ethanol and hydrolysis was performed to give 5-{4-[2-(5-ethyl-2-pyridyl)-2-hydroxyethoxy]benzyl}-2,4-thiazolidinedione in the form of crystals. Yield of 6.2 g. Recrystallization from ethyl acetate-hexane produced colorless prisms. m.p. 129°–130° C.

Elemental analysis, for $C_{19}H_{20}N_2O_4S$: Calcd.: C, 61.27; H, 5.41; N, 7.52. Found: C, 61.36; H, 5.71; N, 7.08.

EXAMPLE 4

A mixture of methyl 2-bromo-3-{4-[2-(5-ethyl-2-pyridyl)-3-hydroxypropoxy]phenyl}propionate (12.2 g), thiourea (2.2 g), sodium acetate (2.4 g) and ethanol (100 ml) was heated under reflux for 3 hours, and 3N-hydrochloric acid (100 ml) was added to the mixture, followed by heating under reflux for 12 hours. After concentration, the reaction mixture was neutralized with aqueous sodium hydrogencarbonate solution and extracted with ethyl acetate. The ethyl acetate layer was washed with water, dried (MgSO$_4$) and then freed of the solvent. The residue was chromatographed on a silica-gel (200 g) column, and elution was effected with benzene-acetone (5:1, V/V) to give 5-{4-[2-(5-ethyl-2-pyridyl)-3-hydroxypropoxy]benzyl}-2,4-thiazolidinedione in the form of an oily substance. Yield of 4.8 g (42.9%). The substance was dissolved in methanol (15 ml), and sodium methylate (28% methanol solution, 2.9 g) was added to the solution, followed by addition of ethyl ether (150 ml) to give the sodium salt in the form of crystals. Yield of 4.8 g (40.7%). Recrystallization from ethanol-ethyl ether produced colorless prisms. m.p. 237°–238° C.

Elemental analysis, for $C_{20}H_{21}N_2O_4S \cdot Na$: Calcd.: C, 58.81; H, 5.18; N, 6.86. Found: C, 59.06; H, 4.94; N, 6.97.

EXAMPLE 5

A mixed solution of 5-{4-[2-hydroxy-2-(6-methyl-2-pyridyl)ethoxy]benzyl}-2,4-thiazolidinedione (350 mg), pyridine (5 ml) and acetic anhydride (0.2 ml) was allowed to stand at room temperature for 2 days, and then poured in water, followed by extraction with ethyl acetate. The ethyl acetate layer was washed with water, dried (MgSO$_4$) and freed of the solvent. The residue was chromatographed on a silica gel (20 g) column, and elution was effected with benzene-acetone (15:1, V/V) to give 5-{4-[2-acetoxy-2-(6-methyl-2-pyridyl)ethoxy]benzyl}-2,4-thiazolidinedione in the form of an oily substance. Yield of 360 mg (89.8%). IR (neat): 1740, 1690, 1230 cm$^{-1}$. NMR (CDCl$_3$)δ: 2.11(3H,s), 2.51(3H,s), 3.02 (1H,dd,J=14 and 9 Hz), 3.41(1H,dd,J=14 and 4 Hz), 4.37(2H,d, J=5 Hz), 4.44(1H,dd,J=9 and 4 Hz), 6.13(1H,t,J=5 Hz), 6.83(2H, d,J=9 Hz), 7.09(2H,d,J=9 Hz), 7.0–7.7(3H,m).

EXAMPLE 6

A mixture of 5-{4-[2-(5-ethyl-2-pyridyl)-3-hydroxypropoxy]benzyl}-2,4-thiazolidinedione sodium salt (408 mg), pyridine (10 ml) and acetic anhydride (0.15 ml) was stirred at room temperature for 8 hours, and poured in water, followed by extraction with ethyl acetate. The ethyl acetate layer was washed with water, dried (MgSO$_4$) and freed of the solvent. The residue was chromatographed on a silica-gel (20 g) column and elution was effected with benzene-acetone (10:1, V/V) to give 5-{4-[3-acetoxy-2-(5-ethyl-2-pyridyl)propoxy]benzyl}-2,4-thiazolidinedione in the form of an oily substance. Yield of 350 mg (81.8%). IR(Neat): 1740, 1690, 1230 cm$^{-1}$. NMR (CDCl$_3$)δ: 1.24(3H,t,J=7 Hz), 2.00(3H,s), 2.64(2H,q,J=7 Hz), 3.03(1H,dd,J=14 and 9 Hz), 3.45(1H,dd,J=14 and 9 Hz), 3.60 (1H,m), 4.31(2H,d,J=5 Hz), 4.47(1H,dd,J=9 and 4 Hz), 4.55 (2H,d,J=5 Hz), 6.80(2H,d,J=9 Hz), 7.10(2H,d,J=9 Hz), 7.20(1H,d, J=8 Hz), 7.48(1H,dd,J=8 and 2 Hz), 8.42(1H,d,J=2 Hz).

EXAMPLE 7–9

By following the same procedure as described in Example 1, there were obtained the following compounds.

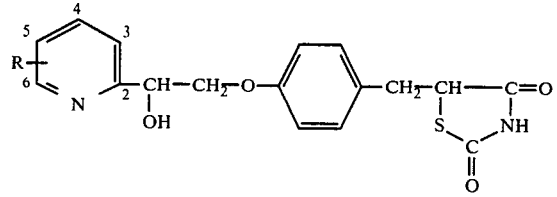

| Example No. | R | melting point (°C.) | Recrystallization solvent | yield (%) |
|---|---|---|---|---|
| 7 | 3-CH$_3$ | 203–204 | DMF-water | 83.8 |
| 8 | H | 162–164 | ethanol | 46.0 |
| 9 | 5-CH$_3$ | 135–137 | ethyl acetate-hexane | 59.8 |

EXAMPLE 10

By following the same procedure as described in Example 4, sodium salt of 5-{4-[2-(4,6-dimethyl-2-pyridyl)-2-hydroxyethoxy]benzyl}-2,4-thiazolidinedione was obtained. Yield: 72.7%. Recrystallization from ethanol-ether produced colorless crystals. m.p. 228°–229° C. Elemental analysis, for $C_{19}H_{19}N_2O_4S \cdot Na$: Calcd.: C, 57.86; H, 4.86; N, 7.10. Found: C, 57.38; H, 4.69; N, 6.96.

EXAMPLE 11

A mixed solution of 5-{4-[2-(5-ethyl-2-pyridyl)-2-hydroxyethoxy]benzyl}-2,4-thiazolidinedione (500 mg), pyridine (5 ml) and propionic anhydride (0.3 ml) was allowed to stand over night at room temperature, and then poured in water, followed by extraction with ethyl acetate. The ethyl acetate layer was washed with water, dried (MgSO$_4$) and freed of the solvent. The residue was chromatographed on a silica gel (30 g) column, and elution was effected with benzene-acetone (15:1, V/V) to give 5-{4-[2-(5-ethyl-2-pyridyl)-2-propionyloxyethoxy]benzyl}-2,4-thiazolidinedione in the form of an oily substance. Yield of 515 mg (89.7%).

IR(Neat): 1745, 1700, 1170 cm$^{-1}$.

NMR (CDC$_3$)δ: 1.13(3H,t,J=7 Hz), 1.23(3H,t,J=7 Hz), 2.40(2H,q,J=7 Hz), 2.31(2H,q,J=7 Hz), 3.02(1H,dd, J=14 and 10 Hz), 3.4(1H,m), 4.38(2H,d,J=5 Hz), 4.40(1H,dd,J=10 and 4 Hz), 6.18(1H,t,J=5 Hz), 6.81(2H,d,J=9 Hz), 7.10(2H,d,J=9 Hz), 7.3~7.6(2H,m), 8.43(1H,d,J=2 Hz), 9.2(1H, broad).

EXAMPLE 12

Example of production of tablets:

| | | |
|---|---|---|
| (1) | 5-{4-[2-(5-ethyl-2-pyridyl)-2-hydroxyethoxy]-benzyl}-2,4-thiazolidinedione | 100 g |
| (2) | Lactose | 50 g |
| (3) | Corn starch | 15 g |
| (4) | Carboxymethylcellulose calcium | 44 g |
| (5) | Magnesium stearate | 1 g |
| | | 210 g for 1000 tablets |

The total amount each of the ingredients (1), (2) and (3) are kneaded with 30 g of the ingredient (4) in the presence of water, and the mixture is vacuum-dried and granulated. The resulting granulates are mixed with 14 g of the ingredient (4) and 1 g of the ingredient (5) and compressed into tablets by use of a tablet compressing machine to manufacture 1000 tablets of 8 mm in diameter each containing 100 mg of the ingredient (1).

REFERENCE EXAMPLE 1

(1) m-Chloroperbenzoic acid (70% of content, 7.1 g ) was added to a solution of methyl 2-bromo-3-{4-[2-(6-methyl-2-pyridyl)ethoxy]phenylpropionate (10.0 g) in methanol (100 ml) and the mixture was heated under reflux for 30 minutes. After aqueous sodium thiosulfate solution was added to decompose the excess oxidizing agent, water was added to the reaction mixture, followed by extraction with ethyl acetate. The ethyl acetate layer was washed successively with water, 2N-potassium hydroxide and water in the mentioned order, dried (MgSO$_4$) and freed of the solvent by distillation to give a crude oily substance of methyl 2-bromo-3-{4-[2-(6-methyl-2-pyridyl)ethoxy]phenyl}propionate N-oxide. Yield of 10.1 g. IR (Neat): 1740, 1250 cm$^{-1}$.

(2) A mixture of methyl 2-bromo-3-{4-[2-(6-methyl-2-pyridyl)ethoxy]phenyl}propionate N-oxide (10.1 g) as obtained under (1) and acetic anhydride (50 ml) was heated at 110° C. for 1 hour and concentrated under reduced pressure, and the residue was chromatographed on a silica-gel (200 g) column. Elution was effected with benzene-acetone (50:1, V/V) to give methyl 3-{4-[2-acetoxy-2-(6-methyl-2-pyridyl)ethoxy]-phenyl}-2-bromopropionate in the form of an oily substance. Yield of 3.3 g. IR (neat): 1740 cm$^{-1}$(broad). NMR (CDCl$_3$)δ: 2.13(3H,s), 2.53(3H,s), 3.14(1H,dd,J=14 and 7 Hz), 3.40(1H, dd,J=14 and 7 Hz), 3.70(3H,s), 4.2–4.5(3H,m), 6.15(1H,t,J=6 Hz), 6.8–7.6(7H,m).

REFERENCE EXAMPLE 2

(1) 60% Oil-borne sodium hydride (2.8 g) was added little by little to a solution of 2-(3-methyl-2-pyridyl)-1,3-propylene glycol (10.0 g) and p-fluoronitrobenzene (8.45 g) in dimethylformamide (100 ml) under ice-cooling with stirring. After stirring under ice-cooling for 1 hour, the reaction solution was poured in ice-cold water, and the aqueous mixture was extracted with ethyl acetate. The ethyl acetate layer was washed with water, dried (MgSO$_4$) and freed of the solvent by distillation, and the residue was chromatographed on a silica-gel (200 g) column. Elution was effected with cyclohexane-ethyl acetate (3:1, V/V) to give 4-[3-hydroxy-2-(3-methyl-2-pyridyl)propoxy]nitrobenzene in the form of crystals. Yield of 9.6 g. Recrystallization from ethyl acetatehexane produced colorless prisms. m.p. 135°–136° C.

Elemental analysis, for C$_{15}$H$_{16}$N$_2$O$_4$: Calcd.: C, 62.49; H, 5.59; N, 9.72. Found: C, 62.60; H, 5.69; N, 9.93.

(2) 4-[3-hydroxy-2-(3-methyl-2-pyridyl)propoxy]nitrobenzene (9.0 g) as obtained under (1) was dissolved in methanol (100 ml), and catalytic reduction was conducted at ambient temperature and at atmospheric pressure with use of 10% palladium-carbon. The catalyst was filtered out, and the solvent was distilled off. Then, the residue was dissolved in a mixture of methanol (80 ml), acetone (20 ml) and 47% aqueous hydrobromic acid (21.5 g), and a solution of sodium nitrite (2.4 g) in water (5 ml) was added dropwise to the solution at a temperature of not higher than 5° C. under ice-cooling, followed by stirring at 5° C. for 30 minutes. Methyl acrylate (15.9 g) was added to the solution, which was then warmed at about 40° C. Cuprous chloride (7.0 g) was added little by little to the mixture with vigorous stirring, and stirring was continued at the reaction temperature maintained at not higher than 45° C. for about 3 hours until the evolution of nitrogen stopped. The reaction solution was concentrated under reduced pressure, and the concentrate was made alkaline with aqueous concentrated ammonia and extracted with ethyl acetate. The ethyl acetate layer was washed with water, dried (MgSO$_4$) and freed of the solvent by distillation. The residue was chromatographed on a silica-gel (230 g) column, and elution was effected with ethyl ether-hexane-triethylamine (75:25:1, V/V) to give methyl 2-bromo-3-{4-[3-hydroxy-2-(3-methyl-2-pyridyl)-propoxy]phenyl}propionate in the form of an oily substance. Yield of 4.8 g. IR (Neat): 3370, 1735 cm$^{-1}$ NMR (CDCl$_3$)δ: 2.35(3H,s), 2.9–3.4(2H,m), 3.3–3.7(1H,m), 3.63(3H,s), 3.9(1H,broad), 4.07 (2H,d,J=3 Hz), 4.1–4.6(3H,m), 6.76(2H,d,J=9 Hz), 7.04(2H,d, J=9 Hz), 7.3–7.6(2H,m), 8.30(1H,dd,J=5 and 2Hz).

REFERENCE EXAMPLE 3

(1) By following the same procedure as described in Reference Example 1-(1), methyl 2-bromo-3-{4-[2-(5-ethyl-2-pyridyl)ethoxy]phenyl}propionate (18.5 g) was oxidized with m-chloroperbenzoic acid to give methyl 2-bromo-3-{4-[2-(5-ethyl-2-pyridyl)ethoxy]phenyl}propionate N-oxide. Yield of 19.2 g.

(2) Methy 2-bromo-3-{4-[2-(5-ethyl-2-pyridyl)ethoxy]phenyl}propionate N-oxide (19.0 g) as obtained in Reference Example 3-(1) was reacted with acetic anhydride in the same manner as described in Reference Example 1-(2), and the resulting product was purified by silica-gel column chromatography to give methyl 3-{4-[2-acetoxy-2-(5-ethyl-2-pyridyl)ethoxy]phenyl}-2-bromopropionate in the form of an oily substance. Yield of 10.2 g. IR (Neat): 1730 cm$^{-1}$. NMR (CDCl$^3$)δ: 1.23(3H,t,J=7 Hz), 2.13(3H,s), 2.66(2H,q,J=7 Hz), 3.12(1H,dd,J=14 and 7 Hz), 3.40 (1H,dd,J=14 and 7 Hz), 3.70(3H,s), 4.33(1H,t,J=7 Hz), 4.40 ((2H,d,J=5 Hz), 6.17(1H,t,J=5 Hz), 6.83(2H,d,J=9 Hz), 7.11 (2H,d,J=9 Hz), 7.33(1H,d,J=8 Hz), 7.54(1H,dd,J=8 and 2 Hz), 8.43 (1H,d,J=2 Hz).

REFERENCE EXAMPLE 4

By following the same procedure as described in Reference Example 2, there were obtained the following compounds:

(1) 4-[2-(5-Ethyl-2-pyridyl)-3-hydroxypropoxy]nitrobenzene: an oily substance, IR (Neat): 3250, 1330 cm$^{-1}$ NMR (CDCl$_3$)δ: 1.23(3H,t,J=7 Hz), 2.63(2H,q,J=7 Hz), 3.35(1H,m), 4.10(2H,d, J=4 Hz), 4.50(3H,m), 6.93(2H,d,J=9 Hz), 7.19(1H,d,J=8 Hz), 7.51(1H,dd,J=8 and 2 Hz), 8.13(2H,d,J=9 Hz), 8.35(1H,d,J=2 Hz).

(2) Methyl 2-bromo-3-{4-[2-(5-ethyl-2-pyridyl)-3-hydroxypropoxy]phenyl}propionate: an oily substance, IR (Neat): 3300, 1730 cm$^{-1}$. NMR (CDCl$_3$)δ: 1.23(3H,t,J=7 Hz), 2.62(2H,q,J=7 Hz), 3.0 to 3.5(3H,m), 3.68(3H,s), 4.09(2H,d,J=4 Hz), 4.2–4.6(3H,m), 6.7–7.6(6H,m), 8.35(1H,d,J=2 Hz).

REFERENCE EXAMPLE 5

By following the same procedure as described in Reference Example 1, there were obtained the following compounds:

methyl 3-{4-[2-acetoxy-2-(2-pyridyl)ethoxy]phenyl}-2-bromopropionate. Oily substance. Yield: 54.4%.

IR (Neat): 1740 cm$^{-1}$.

NMR (CDCl$_3$)δ: 2.14(3H,s), 3.11(1H,dd,J=14 and 7 Hz), 3.38(1H,dd,J=14 and 7 Hz), 3.69(3H,s), 4.33(1H,t, J=7 Hz), 4.40(2H,d,J=5 Hz), 6.17(1H,t,J=5 Hz), 6.80(2H,d,J=9 Hz), 8.08(2H,d,J=9 Hz), 7.2–7.8(3H,m), 8.25(1H,dd,J=5 and 2 Hz).

methyl 3-{4-[2-acetoxy-2-(3-methyl-2-pyridyl)ethoxy]phenyl}2-bromopropionate. Oily substance. Yield: 30.1%

IR (Neat): 1730 cm$^{-1}$.

NMR(CDCl$_3$)δ: 2.09(3H,s), 2.49(3H,s), 3.12(1H,dd, J=14 and 7 Hz), 3.40(1H,dd,J=14 and 7 Hz), 3.70(3H,s), 4.1~4.6(3H,m), 6.33(1H,dd,J=8 and 5 Hz), 6.81(2H,d, J=9 Hz), 8.08(2H,d,J=9 Hz), 7.2~7.6(2H,m), 8.44(1H, dd,J=5 and 2 Hz).

methyl 3-{4-[2-acetoxy-2-(5-methyl-2-pyridyl)ethoxy]phenyl}-2-bromopropionate. Oily substance. Yield: 61.0%.

IR (Neat): 1740 cm$^{-1}$.

NMR (CDCl$_3$)δ: 2.19(3H,s), 2.30(3H,s), 3.10(1H,dd, J=14 and 7 Hz), 3.37(1H,dd,J=14 and 7 Hz), 4.30(1H,t,J=7 Hz), 4.37(2H,d,J=5Hz), 6.12(1H,t,J=5 Hz), 6.79(2H,d,J=9 Hz), 8.06(2H,d,J=9 Hz), 7.2~7.6(2H,m), 8.37(2H,d,J=2 Hz).

methyl 3-{4-[2-acetoxy-2-(4,6-dimethyl-2-pyridyl)ethoxy]phenyl}-2-bromopropionate. Oily substance. Yield: 51.2%.

IR (Neat): 1740 cm$^{-1}$.

NMR (CDCl$_3$): 2.13(3H,s), 2.28(3H,s), 2.47(3H,s), 3.12(1H,dd,J=14 and 7 Hz), 3.38(1H,dd,J=14 and 7 Hz), 3.69(3H,s), 4.31(1H,t,J=7 Hz), 4.37(2H,d,J=5 Hz), 6.10(1H,t,J=5 Hz), 6.7~7.2(6H,m).

EXPERIMENT EXAMPLE

Blood sugar- and lipid-lowering activity in mice.

0.005% of a test compound was mixed with a powder diet (CE-2, produced by CLEA JAPAN), and KKAy mice (male, 8 to 10 weeks of age, 5 mice/group) were placed on the diet for 4 days, and allowed free access to water throughout the experiment. Blood samples were taken from the orbital veins and assayed for blood sugar by the glucose oxidase method and for plasma triglyceride by the enzyme method in which the produced glycerol was determined by means of Cleantech TG-S Kit (Yatron), respectively. The respective values are expressed in terms of rate of lowering (%) from the values of control group not receiving the test compound.

| Test compound (No. of Example) | Hypoglycemic activity (%) | Hypolipemic activity (%) |
|---|---|---|
| 1 | 45 | 47 |
| 2 | 22 | 11 |
| 3 | 32 | 35 |
| 4 | 45 | 38 |
| 7 | 53 | 58 |
| 8 | 47 | 53 |
| 9 | 35 | 19 |
| 10 | 40 | 47 |

INDUSTRIAL AVAILABILITY

The novel thiazolidinedione derivatives (I) according to the present invention exhibit excellent blood sugar- and lipid-lowering activity, and are of value as pharmaceuticals, such as therapeutic agent for diabetes and therapeutic agent for hyperlipemia, and so forth.

We claim:

1. A thiazolidinedione derivative of the formula:

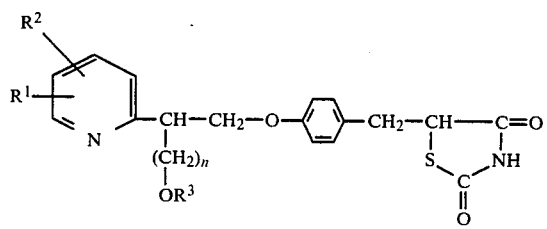

wherein R$^1$ and R$^2$ are the same or different and each represent hydrogen or a lower alkyl group; R$^3$ is hydrogen or formyl, alkylcarbonyl having 2 to 6 carbon atoms, phenylacetyl, phenylpropionyl, benzoyl or p-toluoyl; n is 0 or 1 or a pharmaceutical acid addition salt or a base salt thereof.

2. A blood sugar-and lipid-lowering composition which contains an effective amount of a thiazolidinedione derivative of the formula:

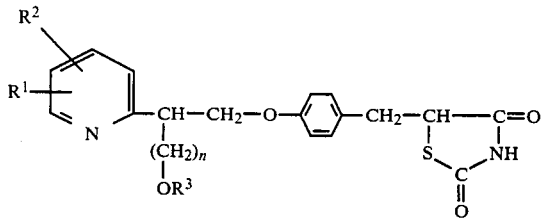

wherein R$^1$ and R$^2$ are the same or different and each represent hydrogen or a lower alkyl group; R$^3$ is hydrogen or formyl, alkylcarbonyl having 2 to 6 carbon atoms, phenylacetyl, phenylpropionyl, benzoyl or p-toluoyl; n is 0 or 1 or a pharmaceutical acid addition salt or a pharmaceutical base salt thereof.

3. The compound as claimed in claim 1, wherein n is zero.

4. The compound as claimed in claim 1, wherein R$^3$ is hydrogen.

5. The compound as claimed in claim 1, wherein the compound is 5-{4-[2-(5-ethyl-2-pyridyl)-2-hydroxyethoxy]benzyl}-2,4-thiaxolidinedione.

6. The compound as claimed in claim 1, wherein the compound is 5-{4-[2-hydroxy-2-(2-pyridyl)ethoxy]benzyl}-2,4-thiazolidinedione.

7. The compound as claimed in claim 1, wherein the compound is 5-{4-[2-hydroxy-2-(6-methyl-2-pyridyl)ethoxyl]benzyl}-2,4-thiazolidinedione.

8. The compound as claimed in claim 1, wherein the compound is 5-{4-[2-hydroxy-2-(3-methyl-2-pyridyl)ethoxy]benzyl}-2,4-thiazolidinedione.

* * * * *